United States Patent [19]
Melzig et al.

[11] Patent Number: 6,146,554
[45] Date of Patent: Nov. 14, 2000

[54] PHOTOCHROMIC NAPHTOPYRANE COLORANTS, METHOD FOR THE PRODUCTION AND USE THEREOF, PHOTOCHROMIC OBJECT

[75] Inventors: Manfred Melzig, Wessling; Claudia Mann; Udo Weigand, both of Munich, all of Germany

[73] Assignee: Optische Werke G. Rodenstock, Munich, Germany

[21] Appl. No.: 09/308,586

[22] PCT Filed: Sep. 22, 1998

[86] PCT No.: PCT/DE98/02820

§ 371 Date: May 21, 1999

§ 102(e) Date: May 21, 1999

[87] PCT Pub. No.: WO99/15518

PCT Pub. Date: Apr. 1, 1999

[30] Foreign Application Priority Data

Sep. 22, 1997 [DE] Germany ............................ 197 41 705
Apr. 27, 1998 [DE] Germany ............................ 198 18 684

[51] Int. Cl.$^7$ .......................... G02B 5/23; C07D 311/92; C08K 5/15
[52] U.S. Cl. .......................... 252/586; 549/382; 549/389; 549/362; 549/60; 549/58; 548/454; 548/525; 548/526; 546/281.1; 546/282.7; 544/148; 544/150
[58] Field of Search ...................... 252/582, 586; 524/110; 549/382, 389, 58, 60, 362; 548/454, 525, 526; 546/281.1, 282.7, 196, 197; 544/148, 150

[56] References Cited

U.S. PATENT DOCUMENTS

| | | | |
|---|---|---|---|
| 5,645,767 | 7/1997 | Gemert | 252/586 |
| 5,698,141 | 12/1997 | Kumar | 252/586 |
| 5,955,520 | 9/1999 | Heller et al. | 524/87 |
| 5,961,892 | 10/1999 | Gemert et al. | 252/586 |

Primary Examiner—Shean C. Wu
Attorney, Agent, or Firm—Evenson, McKeown, Edwards & Lenahan, P.L.L.C.

[57] ABSTRACT

What is described here are photochromic naphthopyrane dyes with different substituents whose properties can be set by controlled selection of the substituents. In this manner it is possible to take an influence on the migration characteristics, the absorption characteristics and the brightening rate and kinetics. The inventive compounds display good darkening and brightening properties at a very good service life.

The invention excels itself by the fact that a method is made available which is substantially improved over prior art, in addition to the surprising influence on specific properties of the inventive compounds. The described compounds are suitable for application in synthetic materials of any kind.

A photochromic object is also the subject matter of the invention, which comprises one or several photochromic naphthopyrane dyes as well as at least one polymer material, with the photochromic object being producible by mass-dyeing or superficial dyeing.

27 Claims, 6 Drawing Sheets

PHOTOCHROMIC NAPHTOPYRANE COLORANTS, METHOD FOR THE PRODUCTION AND USE THEREOF, PHOTOCHROMIC OBJECT

DESCRIPTION

This application is a 371 of PCT/DE98/02820, filed Sep. 22, 1998.

The present invention relates to photochromic compounds, specifically indeno-anellated naphthopyrane dyes with different substituents, to a method of producing same, their application as well as to a photochromic object comprising said photochromic naphthopyrane dyes.

Various dye classes have become known which change their colour reversibly when they are exposed to light of certain wavelengths, in particular sun light. This is due to the fact that supply of energy in the form of light causes these dye molecules to pass over to an excited stage which, when the energy supply is stopped, they leave again for returning into their initial state. These photochromic dyes include, for instance, the naphthopyranes which have been described already with different substituents in prior art.

PRIOR ART

Pyranes, particularly naphthopyranes and major ring systems derived therefrom are that class of photochromic compounds which is predominantly operated on at present. Even though the first patent application was filed for them as early as in 1966 (U.S. Pat. No. 3,567,605) it was possible in the nineties only to develop compounds which appeared to be suitable for the application in spectacle glasses or lenses. One usable class of pyrane compounds are, for instance, the 2,2-diaryl-2H-naphtho[1,2-b]pyranes which, in their excited form, show different hues such as yellow, orange or red-orange. The indeno-anellated naphtopyranes are of interest as another class of photochromic compounds which present an absorption in the range of longer wavelengths due to their larger ring system. It is the systems derived from the 2,2-diaryl-2H-naphtho[1,2-b]pyranes which are produced from the respective naphthopyrane systems by anellation on the f-side.

For instance, the documents WO 96/14596 or the U.S. Pat. No. 5,656,767 disclose indeno[2,1-f]naphtho[1,2-b]pyrane systems, compounds containing these photochromic dyes, as well as a method of producing these compounds. The naphthopyrane systems described in these prior art references are to be modified to the effect that they will achieve a more rapid brightening than the 2H-naphthopyranes so far known. As a solution to this problem only hydrogen and alkyl groups are described by way of example as radicals R at position 13.

The very extensive list of substituents at the aryl or hetero-aryl groups, which is claimed in WO 96/14596 for B and B', mentions piperidine, morpholine and pyrrole in addition to amino, mono- and di-($C_1$–$C_6$)-alkyl amino groups, with details missing:

The aforedescribed compounds can, however, form fulvenes which, in the case of alkyl groups carrying a-hydrogen, are produced with splitting off water. These destructive products of intense colour are formed, inter alia, in the course of the life test (xenon light). Moreover, these photochromic dyes with the substituents claimed in WO 96/14596 or U.S. Pat. No. 5,656,767 can cover only that part of the spectral range which contains the shorter wavelengths, with the colour impression being orange to blue/grey (cf. for instance the description in lines 24/25 on page 2 of WO 96/14596).

Furthermore, in the manufacturing process according to these prior art documents partly highly aggressive reaction conditions are employed, e.g. the materials are heated for one hour with concentrated phosphoric acid at temperatures between 160 and 220° C. (cf. reaction (5): cyclisation from D to E). Consequently, substituents with more sensitive groups are not applicable because they would be oxidised or decomposed under such conditions. In the synthesising approach described in WO 96/14596 or U.S. Pat. No. 5,656,767, respectively, i.e. the closing of the 6-ring before the 5-ring, moreover certain compounds cannot at all be prepared or prepared only with difficulties.

Furthermore, the aforedescribed compounds entail disadvantages because the commercially available lenses containing prior art compounds have a negative effect for the wearer of the glasses because under certain conditions strong colour distortions occur. At very low temperatures and under an intensive ultraviolet radiation, which is the case, for instance, in skiing on glaciers, at least 90% of the incident light are absorbed in the range from 380 to 620 nm. With the absorption undergoing a steep decline towards longer wavelengths (red spectral range), the wearer of the glasses sees the environment with a strong red emphasis (so-called "dark crimson snow").

BACKGROUND OF THE INVENTION

The invention is therefore based on the problem of avoiding the described disadvantages entailed in prior art and to provide photochromic compounds which present properties improved over those of the structures described in prior art and which, in the form excited by light, present a bathochromically shifted absorption in the longest wavelength range within the visible part of the spectrum, compared against comparable prior art compounds. Accordingly compounds had to be found which present a further bathochromic shift of their absorption maximums in the visible range by roughly 100 nm, as compared against the known compounds. Furthermore, the absorption band in the longest wavelength range, i.e. the absorption band between the red or infrared part of the light spectrum and the "absorption gap"—i.e. the point of lowest absorption in the range from 400 to 500 nm—should be as broad as possible. Another objective consisted therefore in the provision of compounds displaying absorption characteristics which offers still a 50% absorption in response to very strong obscuration (transmission at $\lambda_{max}$<10%) at 700 nm and at least a 10% absorption still at 750 nm.

Moreover, the preferred compounds should not present a distinct basic function because experience had shown that these lenses not only tend to add protons and result in colour distortions in the production of photochromic plastic lenses in mass-dyeing processes but in permanent use also tend to give rise to secondary reactions under the influence of light which result in the loss of the photochromic reaction.

Moreover, the method of producing the new compounds should be improved over conventional methods, with a main emphasis on a simple process control, cautious reaction conditions and sound yields.

The above-explained problem of the invention is solved by the photochromic naphthopyrane-dyes having the general formula (I)

(Formula I)

wherein $R_1$ and $R_2$
are equal or different, independently of each other, and are selected from
the group f consisting of $(C_1-C_6)$-alkyl, $(C_1-C_6)$-alkoxy, chloro and fluoro;

or
the group consisting of hydrogen, $(C_1-C_6)$-cyclo-alkyl, phenyl, benzyl, dialkyl-$(C_1-C_6)$-amino, dicyclo-hexylamino, diphenylamino, piperidyl, morpholinyl and pyridyl, with m, n=0, 1 or 2;

or
two $R_1$ and/or two $R_2$ form together, independently of each other, a carbo- or hetero-cyclic ring, selected from benzene, pyridine, pyrazine, pyrimidine, furan and thiophene;

$R_4$
is selected from
the group g consisting of hydrogen, hydroxy, $(C_1-C_6)$-alkyl, $(C_5-C_6)$-cyclo-alkyl, $(C_1-C_6)$-acyl, $(C_1-C_6)$-alkoxy, phenyl, benzyl, mono-substituted phenyl, mono-substituted benzyl, with the aryl substituents being $(C_1-C_6)$-alkyl or $(C_1-C_6)$-alkoxy:

or from
mono-chlorine or mono-fluorine substituted phenyl, naphthyl, phenanthryl, pyrenyl, chinolyl, isochinolyl, benzofuranyl, thienyl, benzothienyl, dibenzofuranyl, dibenzothienyl, carbazolyl or indolyl, each in non-substituted or mono-substituted form, with the substituents being selected from the group consisting of chloro, fluoro, $(C_1-C_6)$-alkyl, or $(C_1-C_6)$-alkoxy;

or from
di- or tri-substituted phenyl, with the substituents being selected form the group consisting of chloro, fluoro, $(C_1-C_6)$-alkyl, $(C_1-C_6)$-alkoxy, $(C_1-C_6)$-$\omega$-phenylalkyl and $(C_1-C_6)$-$\omega$-phenoxy-alkyl, with the phenyl ring at the $\omega$-position possibly representing again the X, X'- or $R_4$ radical of another photochromic pyrane system;

X and X'
are selected, independently of each other, from the group z consisting of (a) and (b), with
(a) the non-, mono-, di- and tri-substituted aryl groups phenyl and naphthyl; and
(b) the non-, mono-, di- and tri-substituted hetero-cyclic groups pyridyl, furanyl, benzofuran-2-yl, benzofuran-3-yl, thienyl, benzothien-2-yl and benzothien-3-yl,
and with the substituents in (a) and (b) being selected from
the group h consisting of hydroxy, amino, mono-$(C_1-C_6)$-alkyl-amino, di-$(C_1-C_6)$-alkylamino, piperidino, morpholino, pyrryl, -$(C_1-C_6)$-alkyl, -$(C_1-C_6)$-chloro-alkyl, -$(C_1-C_6)$-fluoro-alkyl, -$(C_1-C_6)$-alkoxy, mono-$(C_1-C_6)$-alkoxy-$(C_1-C_4)$-alkyl, chloro and fluoro; or the group (a) consisting of non-basic amines such as non-substituted or substituted di-arylamino, pyrazole, imidazole, indole, pyridine, pyrazoline, imidazoline, pyrroline, phenothiazine, phenoxazine, phenazine, acridine, or carbazole, with the substituents on the non-basic amines being selected from $(C_1-C_6)$-alkyl, $(C_1-C_4)$-alkoxy, phenyl, fluoro, chloro and bromo;

or are selected from
(c) $(C_1-C_6)$-alkyl, $(C_1-C_6)$-chloro-alkyl, $(C_1-C_6)$-fluoro-alkyl, mono-$(C_1-C_6)$-alkoxy-$(C_1-C_4)$-alkyl, $(C_3-C_6)$-cyclo-alkyl, mono-$(C_1-C_6)$-alkoxy-$(C_3-C_6)$-cyclo-alkyl, chloro-$(C_3-C_6)$-cyclo-alkyl, and fluoro-$(C_3-C_6)$-cyclo-alkyl;

or
X and X' co-operate with the carbon atoms at the joining site with the pyrane to form a saturated $C_5-C_{10}$-monocyclic, $C_7-C_{12}$-bicyclic or $C_7-C_{12}$-tricyclic hydrocarbon ring or a fluorene-9-ylidene;

or
either X or X' is mono- or di-substituted phenyl which is substituted, in the para position for combination with -phenyl, —$(CH_2)_p$-phenyl or —O—$(CH_2)_p$—O—phenyl (p=1, 2, 3, . . . , 6), with the second phenyl ring forming part of a second—not necessarily identical—photochromic pyrane;

and Y
is selected from the group consisting of hydrogen, $(C_1-C_6)$-alkyl, $(C_1-C_6)$-acyl, non-substituted benzoyl, non-substituted naphthoyl, mono-substituted benzoyl and mono-substituted naphthoyl, with the aryl substituents being $(C_1-C_6)$-alkyl, or $(C_1-C_6)$-alkoxy;

with the condition applying that $R_1$ and $R_2$ are not from the group f if $R_4$ is from the group G and X and X' are from the group z in the event that the radicals of the group z or non-substituted or that the substituents are from the group h.

Overlapping with the closest-coming prior art (WO 96/14596 or U.S. Pat. No. 5,656,767) in terms of the substituents is thus precluded by a Disclaimer.

In accordance with one inventive variant the hetero-cycles in the group $R_4$ in the photochromic naphthopyrane dyes may be combined via the carbo-cycle with the naphthopyrane system, which is not definitely necessary, however, in order to achieve the characteristics which can be attained with the present invention.

In correspondence with one inventive embodiment, photochromic indenoanellated naphthopyranes of the above-shown general chemical formulae are preferred, with $R_1$, $R_2$, $R_4$ and Y being defined as above and with X and X' being selected from the above-identified group z, with the condition applying that $R_1$ and $R_2$ are not from the group f if $R_4$ is from the group g and that X and X' are from the group z in the event that the radicals of the group z are non-substituted or that the substituents are from the group h.

In accordance with the invention $R_4$ may preferably also be selected from the group consisting of phenyl radicals substituted at least in the ortho-position, 1- or 2-naphthyl, 9-phenanthryl, pyrenyl and hetero-aromates such as benzofuranyl, benzothienyl, chinolyl or isochinolyl.

It is preferred in the photochromic naphthopyrane dyes that two $R_1$ and/or two $R_2$, independently of each other, form a hetero-cyclic ring selected from benzene, pyridine, pyrazine, pyrimidine, furan and thiophene.

In correspondence with another embodiment of the invention at least one X or X' may be an above-defined radical from the group z, which is at least substituted with a non-basic amine from the group (a), in the naphthopyrane dyes. X and X' may be the same radicals from the group z with different substituents, e.g. from the group (a). In an alternative, the substituents at X and X' may both be identical. In such a case it is very advantageous that the inventive compounds do not have any basic function in the molecule, which means that they present a very low basicity or no basicity at all. The inventive non-basic amino groups comprise non-substituted or substituted di-aryl amino, pyrazole, imidazole, indole, pyridine, pyrazoline, imidazoline, pyrroline, phenothiazine, phenoxazine, phenazine, acridine, carbazole or the like.

The non-basic amino-substituents of the group (a) may generally be presented in a non-substituted or a mono-substituted form, with the substituents being possibly selected from the group consisting of $(C_1-C_4)$-alkyl, $(C_1-C_4)$-alkoxy, phenyl, fluoro, chloro and bromo. Within the general scope of the present invention it is evident to the expert that any amine whatsoever is an element of group (a), be it an open, i.e. aliphatic, amine or even a cyclic amine, as long as it does not have any distinct basic function.

In distinction from basic amino substituents, inexpedient reactions in the processing of the inventive dyes and even during long-term use under the influence of light are generally precluded when non-basic amino substituents are selected. The service life of the photochromic dyes is hence substantially prolonged, protons are not added, and undesirable colour variations due to secondary reactions do not take place. Moreover, basic amino substituents frequently result in an impairment of the surface nature of the glass during its production by means of mass dyeing, which means that on account of a reduced glass adherence so-called chipping-off occurs. By contrast, the glass adherence is not reduced in the production of mass-dyed glasses when non-basic amino substituents in accordance with the present invention are present so that the number of rejects due to such chip-off is considerably reduced.

It was surprising to find that the characteristics of the inventive naphthopyrane dyes such as absorption, migration and brightening rate may be selectively controlled by the selection of the substituents. Moreover, the molecular weight of the dye can be set and/or multiplied by an appropriate selection of the substituents.

Furthermore, one or several methoxy groups may be present at the 5-, 6-, 7- and/or 8-position of the naphthopyrane ring, i.e. on the naphthalene ring, in the inventive indeno-anellated naphthopyranes. This is a grouping producing a bathochromic effect which produces an additive effect on the groups which are already present and produce a bathochromic effect.

Surprising and unexpected properties become evident particularly when diphenyl amino groups are introduced instead of methoxy groups, for, instance, in the indeno-anellated 2,2-diaryl-2H-naphtho[1,2-b] pyranes:

In the non-substituted 3,3-diaryl-3H-naphtho[2,1-b] pyranes such as those known from the German Patent Application P 198 20 781.6, the substitution of a 4-methoxy group on one of the phenyl rings in the 3-position of the naphthopyrane induces a bathochromic shift of the absorption band in the longest wavelength range by roughly 60 nm due to a di-phenyl amino group.

When 4-methoxy groups are substituted by a di-phenyl amino group at the phenyl rings in the 2-position of the indeno-anellated 2,2-diaryl-2H-naphtho[1,2-b]-pyranes therefrom green compounds with an absorption maximum ranging around 630 nm are expected. The substitution, by contrast, produces only a bathochromic shift by barely 30 nm. In return, the absorption band gains in width substantially; it satisfies the defined absorption conditions in the red range of the visible spectrum range. A second absorption line around 440 nm undergoes a bathochromic shift by roughly 60 nm and now forms a shoulder relative to the main band.

Other particularly preferred photochromic naphthopyrane dyes display the following chemical formula (II):

Formula (II)

wherein $R_1$, $R_2$, m and n have the same definitions as above, $R_5$ represents the substituents defined for $R_4$=phenyl with o=0, 1, 2 or 3, and $R_3$ is a non-basic amine from the above-defined group (a).

In formula (II) the non-basic amino substituent is preferably a non-substituted or substituted diaryl amino, wherein at least one aryl ring may be mono-, di- or tri-substituted. The substituents coming into question here are $(C_1-C_4)$-alkyl, $(C_1-C_4)$-alkoxy, phenyl, fluoro, chloro or bromo.

Preferred inventive naphthopyrane dyes are:

(1) 6-methoxy-3-(4-methoxyphenyl)-3,13-diphenyl-13-hydroxy-benz[p]-indeno [2,1-f]naphtho[1,2-b]pyrane (2) 6-methoxy-3-(4-methoxyphenyl)-3-phenyl-13-(2,5-dimethylphenyl)-13-hydroxy-benz[p]indeno[2,1-f] naphtho[1,2-b]pyrane, (3) 3-(4-diphenyl amino phenyl)-3-phenyl-13-(2,5-dimethylphenyl)-13-hydroxy-benz[p]indeno[2,1-f] naphtho[1,2-b]pyrane, (4) 3-(4-diphenyl amino phenyl)-6-methoxy-3,13-diphenyl-13-hydroxy-indeno[2,1-f]naphtho-[1,2-b] pyrane, (5) 3-(4-diphenyl amino phenyl)6-methoxy-3-phenyl-13-(2,5-dimethylphenyl)-13-hydroxy-indeno[2,1-f] naphtho[1,2-b]pyrane, (6) 6-methoxy-3-(4-methoxy phenyl)-3-phenyl-13-(2,5-dimethylphenyl)-13-hydroxy-indeno[2,1-f]naphtho[1,2-b]pyrane, (7) 6-methoxy-3-(4-methoxyphenyl)-3-phenyl-13-(1-naphthyl)-13-hydroxy-indeno [2,1-f]-naphtho[1,2-b] pyrane, (8) 6,11-dimethoxy-3-(4-methoxyphenyl)-3-phenyl-13-(2,5-dimethyl phenyl)-13-hydroxy-indeno[2,1-f] naphtho[1,2-b]pyrane, (9) 3-(4-methoxyphenyl)-3-phenyl-13-(2,5-dimethylphenyl)-13-hydroxy-indeno-[2,1-f]-naphtho [1,2-b]pyrane, and (10) 6-methoxy-3-(4-methoxyphenyl)-3-phenyl-13-(3-methyl-2-thienyl)-13-hydroxy-indeno[2,1-f]naphtho[1,2-b]pyrane.

Figure 1A:
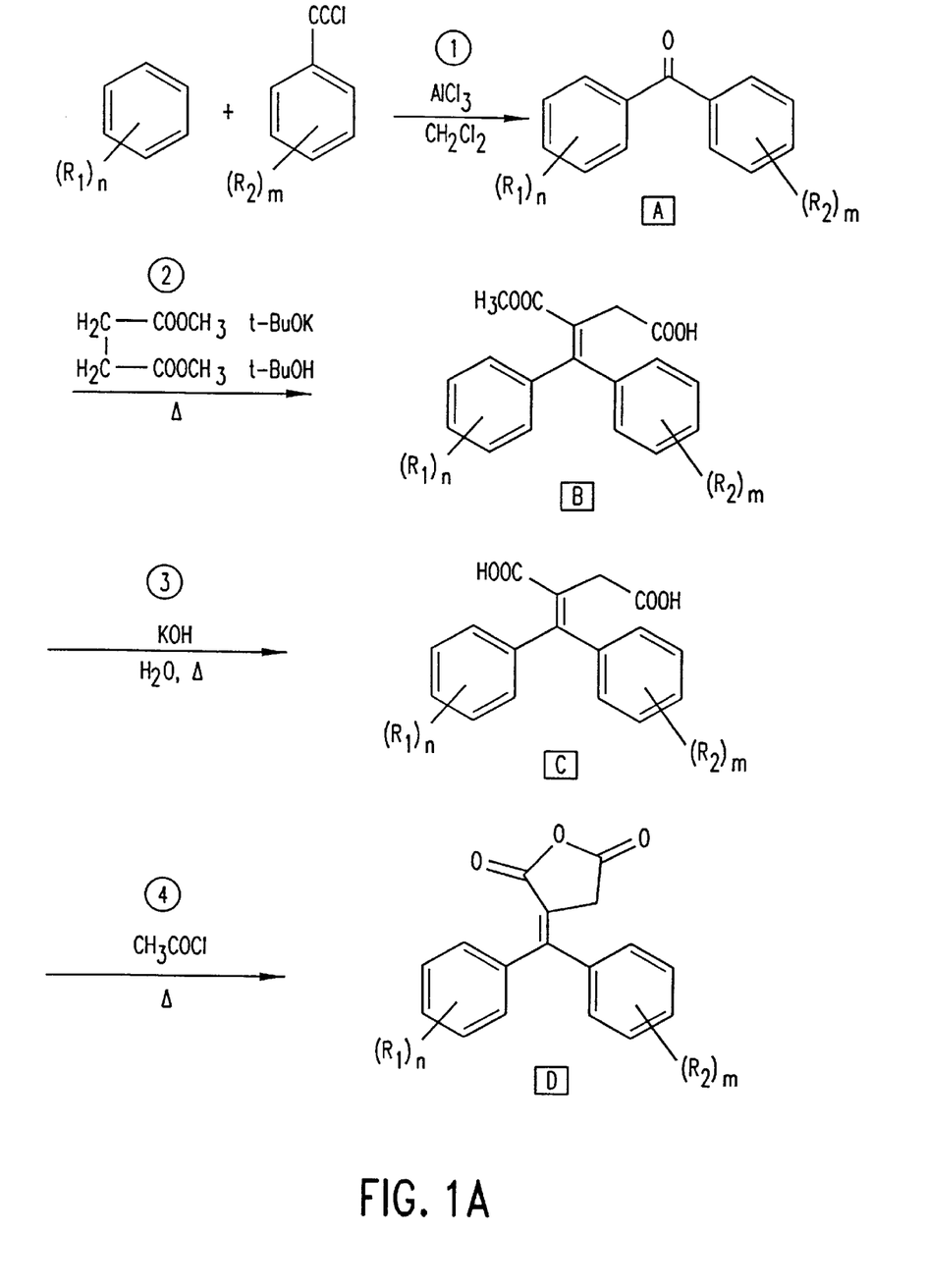
FIGS. 1 and 2 are diagramatic views illustrating the synthesis of photochromic naphthopyran dyes according to the present invention.
Figure 1B:
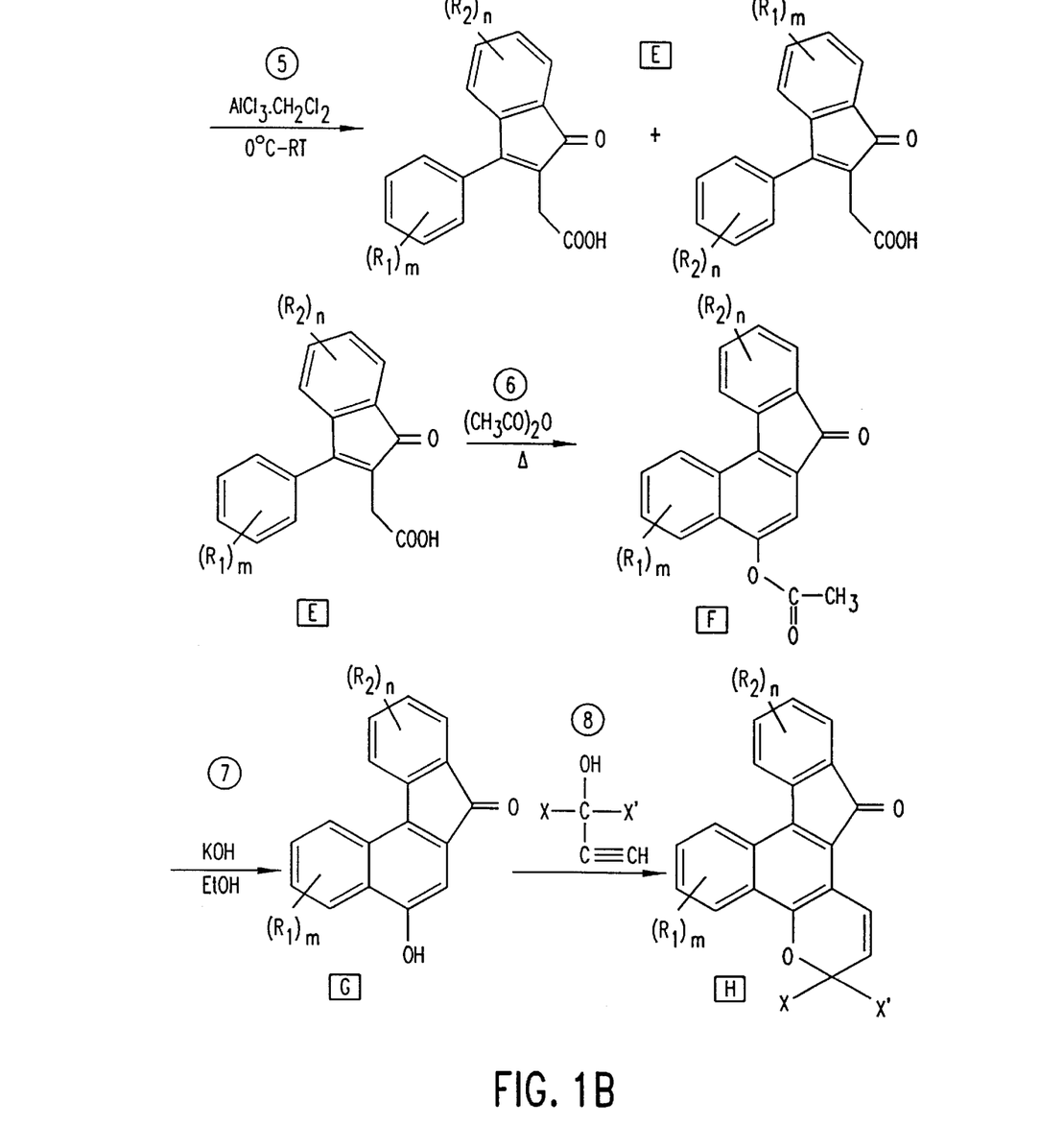
Figure 2:
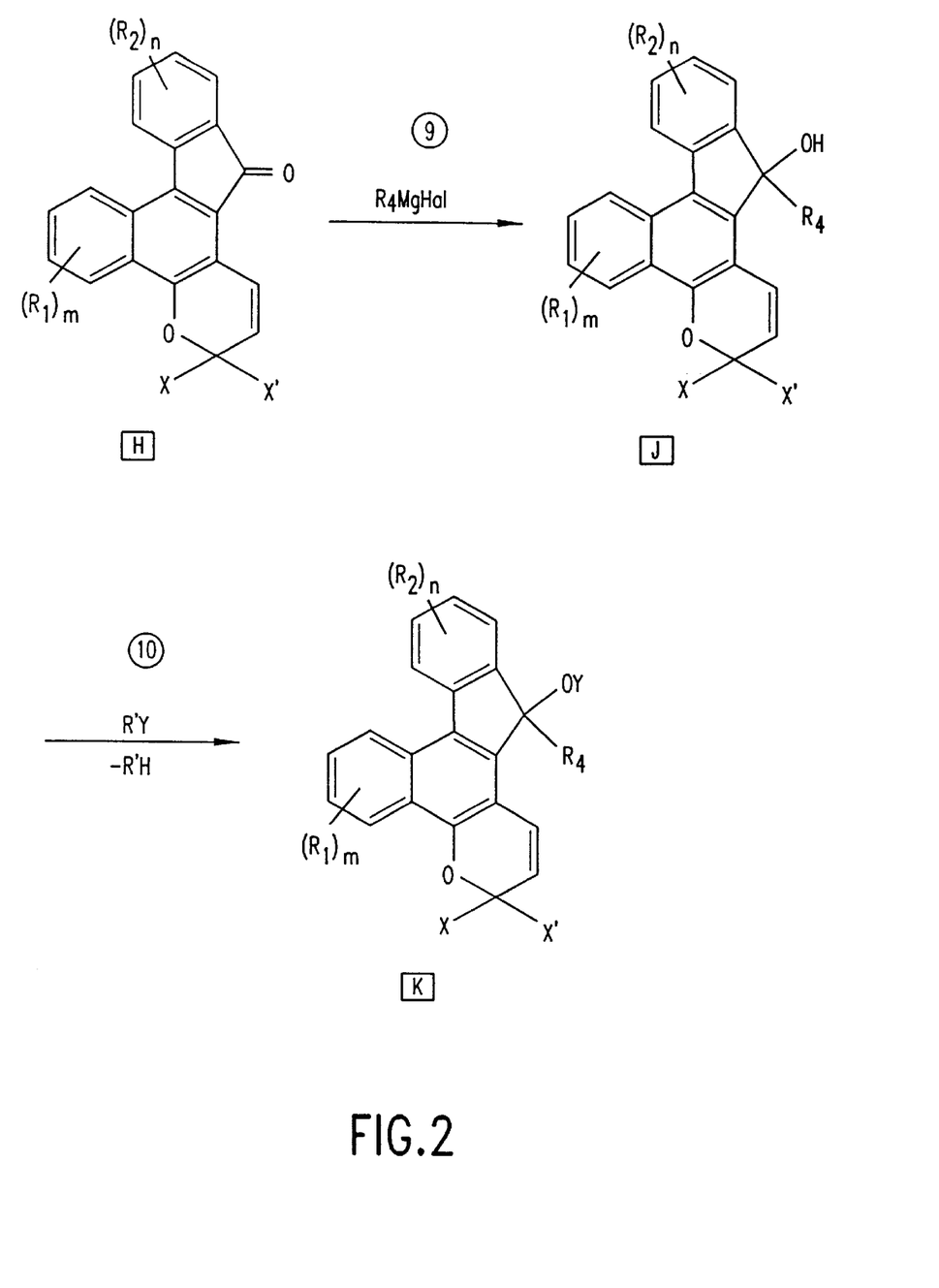

The subject matter of the invention is also a method of producing the inventive photochromic naphthopyrane dyes. With reference to FIGS. 1 and 2 the synthesis operation will be explained in the following in details, with reference being made to the designations used there.

The substituted or non-substituted benzo or naphthophenones employed as starting material are either commercially available or may be easily obtained from the Friedel-Crafts acylation according to step (1), mostly with appropriate yields.

In step (2) the semi-ester B is produced through a Stobbe condensation by means of succino-diester. If the two rings joined via the keto group are not identical a mixture of isomers is created. In variation from the disclosure in WO 96/14596 the operation is continued with the isomer mixture in accordance with the invention. The separation of the honey-like, mostly non-crystallising isomers is very expensive but with the inventively selected synthesising approach it is very easy to perform later on.

Then the semi-ester mixture is saponified with an aqueous alkali according to step (3) so as to form the isomeric mixture of the di-acids C. Then, with separation of water, the isomer mixture of the cyclic anhydrides D is produced in step (4) by heating with acetyl chloride.

In step (5) the isomer mixture E is synthesised with aluminium chloride by intramolecular 5-ring cyclisation. These compounds easily crystallise very well and in the majority of cases they are easy to split into the two isomers on account of their different solubilities in benzene.

Under the influence of acetanhydride the ester F is produced from the desired isomer by intramolecular 6-ring cyclisation according to step (6). This ester is subsequently subjected to alkali saponification in step (7) so as to form the hydroxyfluorenone derivative G.

The reaction with a 2-propine-1-ol derivative (step (8)) results in the weakly photochromic indeno-anellated naphtopyranes H with a strong crimson colouring. This reaction will not be described here in more details because it may be performed in a manner analogous to the production of the 1- or 2-naphtholenes. Examples may be found, inter alia, in the U.S. Pat. Nos. 5,066,818 and 5,238,981 and in the European Patent EP 0 246 114.

The compounds J are then produced in step (9) using appropriate Grignard compositions. Their free hydroxyl group can then also be derivated according to step (10) to form the class of compounds K.

Compared against the method recommended in WO 986/14596 or the U.S. Pat. No. 5,656,767 the aforedescribed synthesising approach presents various advantages:

Firstly, various compounds cannot be synthesised by the method described in WO 986/14596 or the U.S. Pat. No. 5,656,767. The inventive way described here is substantially more cautious; for instance the heating with concentrated phosphoric acid to more than 190° C. is omitted. As a result, even more sensitive groups may be used as substituents $R_1$ and $R_2$. The closing of the 5-ring prior to the 6-ring in the inventive method equally results frequently in products which cannot be synthesised, or with difficulties only, by the prior art approach—closing the 6-ring before the 5-ring. On the other hand, even with the same final product intended, e.g. with symmetric benzo phenones as starting material, less secondary products are produced in accordance with the inventive method described here, whilst purification is easier and the yields of the photochromic dye are higher.

The photochromic naphthopyrane dyes may preferably contain several photochromic colour centres in the molecule, with the further photochromic colour centre absorbing in a range of shorter or longer wavelengths than the photochromic colour centre already existing. For instance, in the inventive method the Grignard reagent, which is used in the reaction of the dyne H in step (9), or the 2-propine-1-ol derivative which is used to react the dye G in step (8), may each contain a photochromic compound.

The precise synthesis approach is described in an exemplary form in the explanation of the examples.

The subject matter of the invention is also the use of the inventive naphthopyrane dyes. These may be used in synthetic materials of any kind and of any shape for a great multitude of applications for which the photochromic properties are important, such as in lenses, protective glasses, sighting shields in protective helmets, windows, spectacle glasses, protective screens, covers, roofs, or the like.

Furthermore, the invention relates also to a photochromic object comprising, inter alia, one or several of the inventive photochromic naphthopyrane dyes as well as at least one polymer material.

Examples of the polymer material used in the photochromic object are poly($C_1$–$C_{12}$-alkyl methacrylates), poly(oxyalkylene dimethacrylates), poly-alkoxylated phenol methacrylates, cellulose acetate, cellulose tri-acetate, cellulose acetate propionate, cellulose acetate butyrate, poly(vinylacetate), poly(vinyl alcohol), poly-(vinylchloride), poly(vinylidene chloride), thermoplastic polycarbonates, polyester, polyurethanes, poly(ethylene terephthalate), polystyrene, poly(ethylene terephthalate), polystyrene, poly($\alpha$-methyl styrene), co-poly(styrene methyl methacrylate), co-poly(styrene acrylonitrile), polyvinyl butyral). Moreover, polymers of the following monomers may be used as well: polyol(allyl carbonate) monomers, polyfunctional acrylate monomers, polyfunctional methacrylate monomers, di-ethylene glycol di-methacrylate monomers, ethoxylated bisphenol-A-di-methacrylate monomers, di-isopropenyl benzene monomers, ethylene glycol bis-methacrylate monomers, poly(ethylene glycol)-bis-methacrylate monomers, ethoxylated phenol methacrylate monomers, alkoxylated poly-alcohol acrylate monomers and di-allylidene penta-erythritol monomers.

In accordance with the invention, the polymer material may be a solid or a transparent homo- or copolymer selected from the group consisting of poly(methyl methacrylate), poly(ethylene glycol bis-methacrylate), poly(ethoxylated bisphenol-A-dimethacrylate), thermoplastic polycarbonate, poly(vinylacetate), polyvinylbutyral, polyurethane or a polymer selected among the elements of the group consisting of di-ethylene glycol bis-(allyl carbonate) monomers, di-ethylene glycol di-methacrylate monomers, ethoxylated phenol methacrylate monomers, di-iso propenyl benzene monomers and ethoxylated tri-methylol propane tri-acrylate monomers.

In accordance with one inventive embodiment the photochromic object may contain at least one further organic photochromic dye in addition to one or several of the aforedescribed polymer materials and at least one inventive photochromic naphthopyrane dye. This further dye preferably presents at least one activated absorption maximum in the range from roughly 400 to 700 nm.

The photochromic object may contain the photochromic naphthopyrane dye or dyes in a quantity from roughly 0.05 to 2.5 mg per cm² of the polymer material surface in which the photochromic dye or dyes are embedded or on which they are applied.

The inventive photochromic naphthopyrane dyes may generally be applied on or embedded into a polymer material such as an organic synthetic material by various methods described in prior art in order to obtain the photochromic object according to the present invention. Here a distinction is made between so-called mass-dyeing and surface-colouring methods.

A mass-dyeing method comprises, for instance, the dissolution or dispersion of the photochromic compound or compounds in a synthetic material, e.g. by the addition of the photochromic compound(s) to a monomer material before the polymerisation takes place. Another possibility of producing a photochromic object is the penetration of the synthetic material or materials with the photochromic compound(s) by immersion of the synthetic material into a hot solution of the photochromic dye or dyes or, for instance, also a thermo transfer process. In correspondence with another variant of the method the photochromic compound may be provided in the form of a separate layer between contiguous layers of the synthetic material, e.g. as part of a polymer film. Moreover, it is also possible to apply the photochromic compound(s) as part of a coating applied on the surface of a synthetic material.

In this context, the expression "penetration" should be understood to denote the migration of the photochromic compound(s) into the synthetic material alone, be it by the solvent-assisted transfer of the photochromic compound(s) into a porous polymer, vapour phase transfer or any other process of superficial diffusion of this type. The photochromic objects according to the invention, such as spectacle glasses, can expediently be produced not only by means of the common mass-dyeing process but equally also by means of superficial coloration, with the latter variant being suitable to achieve a surprisingly reduced migration tendency. This is an advantage particularly in the subsequent enhancing operations because—e.g. in the case of an anti-reflection coating due to the lower re-diffusion in vacuum—a detachment of layers and similar defects are drastically reduced.

On the whole any compatible (i.e. compatible in chemical terms and in terms of colour) coloration—i.e. dyes—whatsoever may be applied on or embedded in the synthetic material in order to satisfy both aesthetic aspects and also medical or fashion requirements. The specifically selected dye or dyes may accordingly vary as a function of the intended effects and requirements.

The properties of the inventive compounds will now be explained with reference to some specific compositions, of course without any restriction of the invention to these embodiments. The special properties of the molecular structures claimed in accordance with the invention may be present separately or in combinations in the form of the specific variations which will be explained in the following, which means that the desired characteristics can be appropriately set and varied and may be present as isolated properties or at the same time.

(a) Inventive 2H-naphthopyranes with non-basic amino substituents

The excellent properties of the inventive indeno-anellated 2H-naphthopyranes, substituted with non-basic amino substituents, become evident in the production of synthetic photochromic lenses. Acid traces which occur in the hydrolysis of the casting resin do not attack these amino compounds. Moreover, in a comparison the compounds present a definitely better service life than the basic amino compounds known from prior art. Another advantage of the existence of non-basic amino compounds is the fact that the glass adherence is not reduced, as has been described above, so that there will not be any impairment of the surface quality, e.g. by so-called chipping off.

Synthetic lenses were produced by way of mass-dyeing, which contained each a quantity of 500 ppm of an inventive compound and of a prior art compound. The compounds had the following structures:

| Substituent | Example | Prior art |
|---|---|---|
| $R_3 = -OCH_3$ | 5 | yes |
| $-NPh_2$ | 10 | no |

Figure 3:
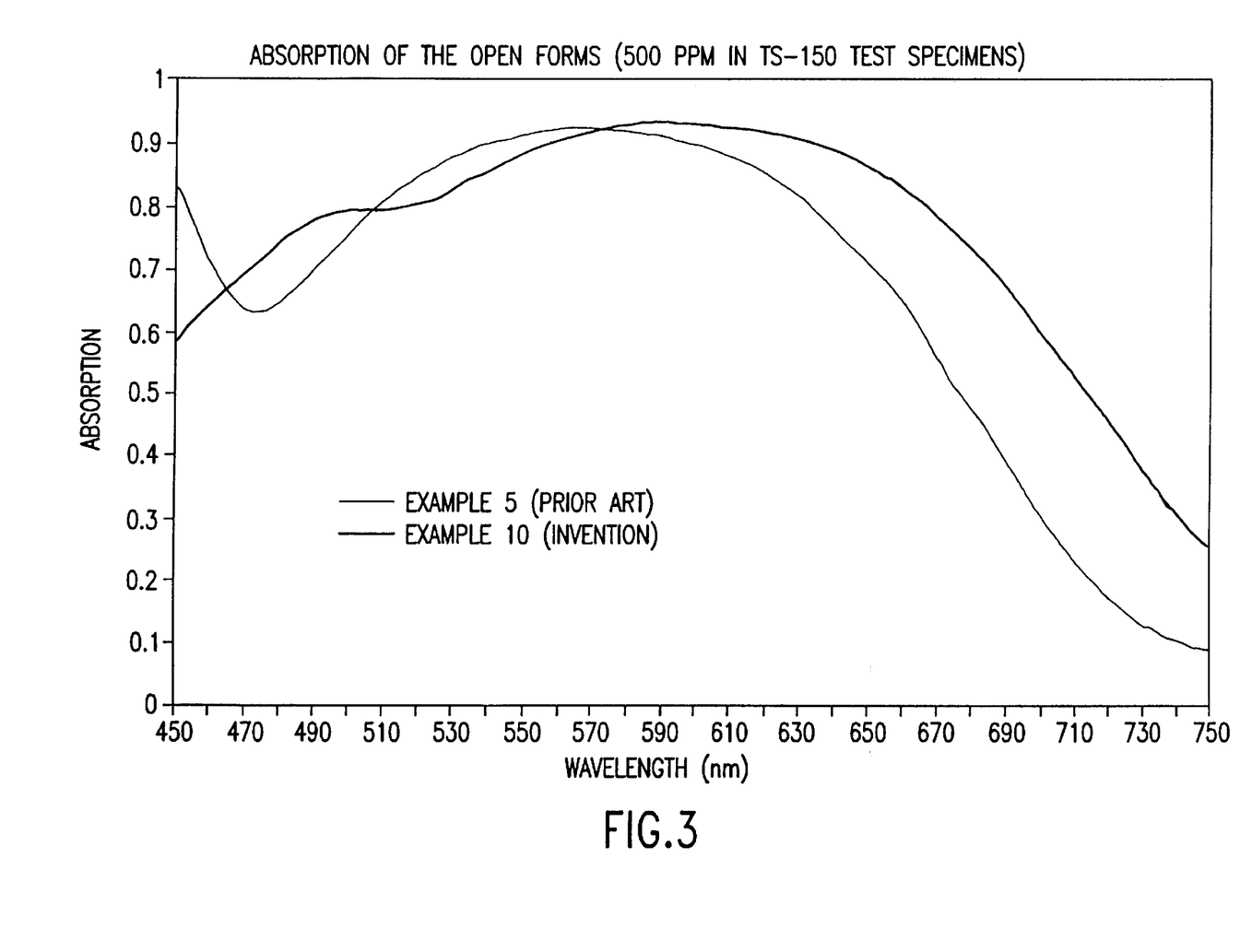
FIGS. 3 through 5 are charts showing absorption spectra of compounds according to the present invention compared to the absorption spectra of various prior art compounds.

Then absorption spectra were recorded of both compounds under identical conditions. The absorption spectra are illustrated in FIG. 3. FIG. 3 shows a comparison of the absorption bands in the visible range between the compound according to prior art and the inventive compound. The compounds shown in FIG. 3 are 13-hydroxy-6-methoxy-3-(4-methoxy phenyl)-3,13-diphenyl indeno[2,1-f]-naphtho[1,2-b]pyrane and 13-hydroxy-6-methoxy-3-(4-diphenyl aminophenyl)-3,13-diphenyl-indeno[2,1-f]naphtho[1,2-b] pyrane.

This documents that the compounds have an absorption maximum at a bathochromic shift in the visible range so that they present excellent absorption characteristics. The absorption band of the longest wavelength, i.e. the absorption band between the red or infrared part of the light spectrum and the "absorption gap"—i.e. the site of lowest absorption within the range 400–500 nm—is very large in accordance with the invention. With very intense obscuration (transmission at $\lambda_{max} < 10\%$) at 700 nm amounts still to at least 50% and at 750 nm to at least 10% absorption so that the inventive indeno-anellated 2H-naphthopyranes are by far superior to the compounds known from prior art.

(b) Inventive benzindeno-anellated naththopyranes

Figure 4:
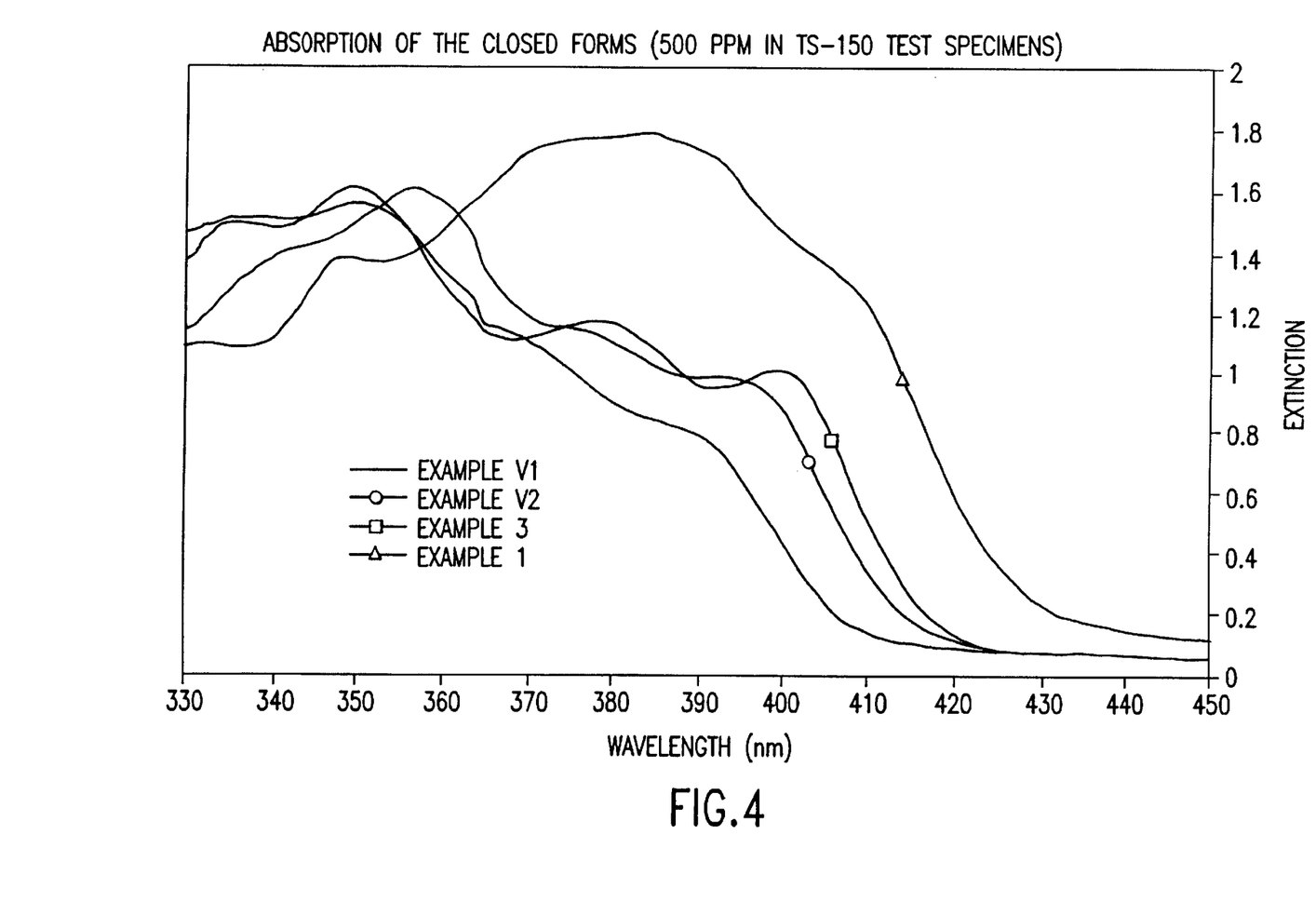
Figure 5:
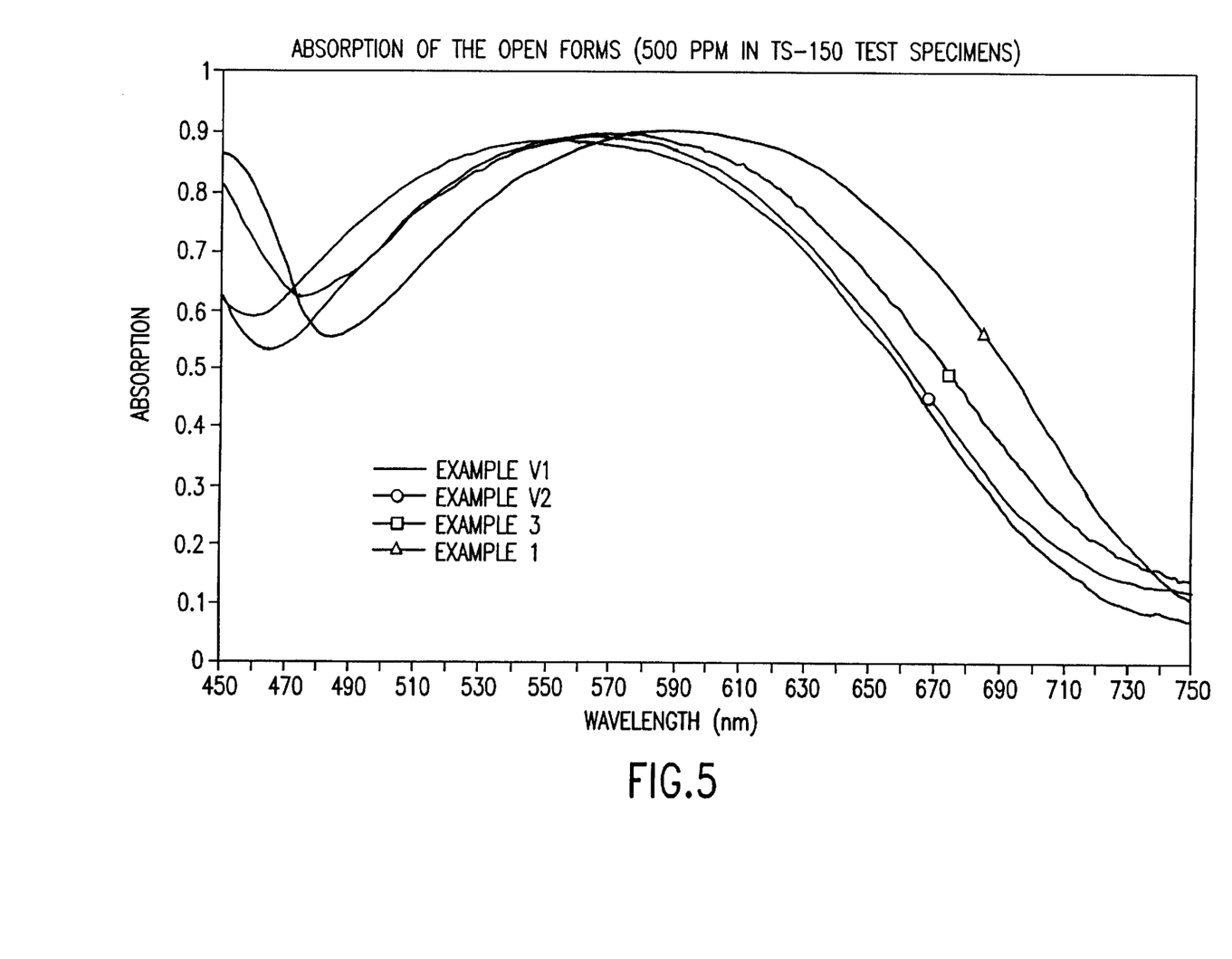

The application of naphtho- instead of benzo-phenones as original compounds A surprisingly resulted in compounds absorbing in the range of major wavelengths, both with the closed form (not excited; cf. FIG. 4) and with the open (excited) form (cf. FIG. 5).

The distinct bathochromic shift and the drastic increase of the coefficient of absorption of the absorption band in the longest wavelength range with the closed form cannot even be expected by the expert since due to the twisting of the two ring systems by steric inhibition of the H-atoms—as in the annellated phenyl ring—the annellated naphthyl ring should at best produce a low inductive effect. The absorption of the longest wavelengths is caused now as before by the naphthopyrane rather than by the naphthalene system. With the spectral intensity of radiation by the sun on the earth surface in the range from 360 to 410 nm increases to 2.88 times the initial value towards the longer wavelengths (EN 1836, Table C.1) this effect is of particular importance specifically for the application in phototropic spectacle lenses.

Equally surprising is the bathochromic shift of the absorption of the open form. Molecules with this structural unit absorb already in a range reaching far into the red spectral range of visible light so that the colour impression is green. With the compounds according to prior art, by contrast—as has been described only—only the spectrum part with the shorter wavelengths is accessible, with the colour impression being orange to blue/grey.

For illustration of the aforedescribed bathochromic shift of the inventive compounds, compared against prior art, comparative tests have been carried out. The results are summarised in Table 1 below.

The first three compounds in Table 1—V1, V2 and Example 3—correspond to prior art (cf. WO 96/14596; the production of V1 and V2 is described there in details.

The production of the test specimens and the measuring methodology are described in details i the Examples.

FIGS. 4 and 5 show the absorption of the closed form or the absorption of the open form, compared against the absorption of the prior art compounds V1 and V2, expressed by plotting the extinction versus the wavelength. For a better recognition of the bathochromic shift a normalisation of the absorption intensity to roughly the same value has been made in the open form.

as to obtain the Grignard and when then naphthopyranes of the structure H are reacted with two equivalents a symmetric double molecule is created. It is likewise possible, however, to react an appropriately substituted phototropic compound of another structure, e.g. a spiro-oxazine or a naphthopyrane absorbing in the range of shorter wavelengths, to form the Grignard and to react it with the naphthopyranes of the structure H to form novel compounds. When this second photochromic compound is so selected that its absorption maximum just registers with the "absorption gap" around 470 nm very dull, almost neutral colours (grey—brown) are achieved in a molecular structure. The advantages of such compounds are described already in the German Patent DE 43 21 487. By a duplication via the substituent X or X', respectively, and a subsequent repeated duplication via a bifunctional Grignard tetra-systems with molecular weights higher than 2000 are achievable.

(d) Brightening rate of the inventive naphthopyranes

It has been found in accordance with the present invention that the application of sterically demanding aromatic radicals as $R_4$ is accompanied by a significant and unexpected increase of the brightening rate. At the same time the formation of fulvenes, which may be produced on alkyl groups carrying α-hydrogen, with separation of water, is made impossible so that these intensively coloured destructive products can no longer occur.

When an alkyl radical $R_4$, as described in WO 96/14596, is substituted by phenyl in accordance with this invention this substitution furnishes the afore-described advantage in terms of stability (no formation of fulvenes). The accelerated

TABLE 1

Absorption maximums of the open and closed forms, starting out from the compound of the general formula (cf. FIGS. 4 and 5):

| Example | substituents | | | | $\lambda_{max}$ (nm) closed form | $\lambda_{max}$ (nm) open form | colour |
| --- | --- | --- | --- | --- | --- | --- | --- |
| | $R_1$ | $R_2$ | $R_3$ | $R_4$ | | | |
| V1 | H | H | $OCH_3$ | H | 350 | 555 | violet |
| V2 | $CH_3$ | $CH_3$ | $OCH_3$ | H | 350, 375 (shoulder) | 570 | blue-violet |
| 3 | $OCH_3$ | H | H | H | 360, 375 (shoulder) | 575 | blue |
| 1 | $OCH_3$ | benzo | H | H | 385 | 600 | green |

(c) Inventive compounds containing several photochromic colour centres

Even though these ring-annellated naphthopyranes display a lower tendency to migrate than common naphthopyranes due to their molecular structure (cf. for instance U.S. Pat. No. 5,369,158) this tendency can even be further reduced by doubling the molecular weight.

This may be done in two ways, either via the component X or X', as disclosed already in WO 96/01884, or via a suitable reaction partner R.

When, for instance, 1,2-bis-(4-bromophenyl)-ethane or 1,2-bis-(4-bromophenoxy)-ethane is reacted on both sides so brightening becomes evident, however, only when more bulky aryl groups are used. The introduction of ortho-substituents into the phenyl rings on X or X', respectively, results in a strong decrease of the brightening rate, as is described in the U.S. Pat. No. 5,066,818. The introduction of ortho-substituents into the phenyl radical $R_4$ leads, by contrast, surprisingly to the contrary, an increase of the brightening rate. Here multiply substituted phenyl radicals or their analogous aryl radicals such as 1- or 2-naphthyl, 9-phenanthryl, pyrenyl and hetero-aromates such as benzofuranyl, benzothienyl, chinolyl or isochinolyl are particularly preferred here.

This effect is all the more surprising as the introduction of more and more bulky radicals does not produce a recognisable effect in the alkyl series, as may be seen in Table 2.

TABLE 2

Brightening rate measured in the polymer CR 307 of the company PPG from WO 96/14596, p. 33

| $R_4$ | Brightening rate $T_{1/2}$ in sec. |
|---|---|
| —$CH_3$ | 362 |
| —$CH_2$—$CH_3$ | 237 |
| —$CH(CH_3)_2$ | 264 |
| —$C(CH_3)_3$ | 313 |

For a further illustration of the foregoing explanations comparative tests have been carried out again on the inventive compounds and on known compounds. The compounds used are derived from the compound of the following general formula:

The brightening rate and the brightening kinetics were measured for differently substituted systems in the polymer Transhade-150 of the company of Tokuyama at different temperatures. The results obtained are summarised in the following, with the following terms being used:

Δ=relative brightening within 10 minutes at 23° C.
=100% (τ10 min–τs)/(τ0–τs)
  τs is the transmission achieved after 15 min of obscuration
  τ0 is the transmission in the fully brightened condition
  τ10 min is the transmission after 10 min brightening in the dark
$T_{1/2}$=time elapsing up to a brightening level corresponding to half the darkening level (half-period)

The brightening kinetics of differently substituted systems was determined, with $R_1$, $R_2$ and $R_3$ representing either the methoxy group or hydrogen; the measurements were performed at 23° C. and 40° C. Three series of tests were measured with variable $R_4$; the results are summarised in the following tables 3 to 5.

TABLE 3

Substituents: $R_1$ = $OCH_3$; $R_2$ = $R_3$ = H

| Substituent | | Example | Δ(10 min, 23° C.) | $T_{1/2}$ (40° C.) |
|---|---|---|---|---|
| $R_4$ = | —$C_2H_5$ | 4 | 25% | 7.0 min |
| | —$C_6H_5$ | 5 | 22% | 7.0 min |
| | -1-naphthyl | 6 | 29% | 5.0 min |
| | -o-tolyl | 7 | 34% | 4.2 min |
| | -2-p-xylyl | 8 | 36% | 4.0 min |
| | -3-methyl-2-thienyl | 9 | 38% | 3.4 min |

TABLE 4

Substituents: $R_1$ = $R_3$ = $OCH_3$; $R_2$ = H

| Substituent | | Example | Δ(10 min, 23° C.) | $T_{1/2}$ (40° C.) |
|---|---|---|---|---|
| $R_4$ = | —$C_4H_9$ | V1 | 40% | 2.7 min |
| | —$C_6H_5$ | V3 | 43% | 2.5 min |
| | -1-naphthyl | V4 | 44% | 2.5 min |
| | -o-tolyl | 16 | 44% | 2.2 min |
| | -2-p-xylyl | 17 | 51% | 2.0 min |

TABLE 5

Substituents: $R_1$ = $R_2$ = H; $R_3$ = $OCH_3$

| Substituent | | Example | Δ(10 min, 23° C.) | $T_{1/2}$ (40° C.) |
|---|---|---|---|---|
| $R_4$ = | —H | 4 | 25% | 7.0 min |
| | —$CH_3$ | 55 | 22% | 7.0 min |
| | —$C_4H_9$ | 6 | 29% | 5.0 min |
| | —$C_6H_5$ | 7 | 34% | 4.2 min |
| | -2-p-xylyl | 8 | 36% | 4.0 min |

The Examples V1, V3, V4, 4, 5, 7, 11 as well as 12, 14, and 16 correspond to prior art, with the presentations of V1, V3 and V3 being described expressis verbis in the document WO 96/14596.

In conclusion it is evident from the foregoing Tables 3 to 5 that in all three series of tests the introduction of ortho-substituents in the aryl radical $R_4$ entails a significant increase of the brightening rate.

In the following now the production of the individual inventive naphthopyrane dyes will be explained in details with reference to Examples, which examples do not limit, of course, the scope of protection of the present invention but are rather merely intended to illustrate the invention.

EXAMPLE 1

(i) Aluminium chloride (40 g) is suspended in a 1 l flask, which is well cooled in an ice bath, in roughly 400 ml dichloro methane while stirring. Then molten 2-naphthoyl chloride/50 g; melting point 50° C.) is slowly added by pouring in a thin stream and the mixture is allowed to be stirred for 5 min (in the ice bath). Then a mixture of anisole (27 g) and 50 ml dichloro methane is added by dropping and the reaction mixture is allowed to thaw over night while being stirred. The next day the mixture is poured, while being stirred, onto 200 g of ice/500 ml water. Stirring is continued for 10 minutes and then the organic phase is isolated in the separating funnel. This phase is extracted twice with water and dried over sodium sulphate. After distillation of the solvent the remaining oil crystallises when it is allowed to stand. After re-crystallisation from roughly 500 ml of boiling methanol achromatic crystals are obtained (58 g) which were identified as 2-(4-methoxy benzoyl) naphthalene by means of the NMR spectrum.

(ii) tert. butanol is melted in advance in a warm water bath. Potassium-tert. butylate (30 g) is suspended in a 1 l three-neck flask in 600 ml ter. butanol and the above-mentioned reaction product as well as succinic dimethyl ester (45 g) are added. The mixture is stirred well and heated with reflux for 1 hour. Then potassium-tert. butylate (30 g) as well as succinic dimethyl ester (45 g) are added again and the mixture is allowed to heat with reflux for 2 hours. After cooling hydrolysis is performed with 2 l of water altogether. Then the mixture is stirred and acidified with concentrated hydrochloric acid. Subsequently the product is extracted twice with 400 ml diethyl ether each, and the combined ether phases are rinsed once with 400 ml of water. Then the mixture is extracted with 500 ml of saturated sodium hydrogen carbonate solution. The product thereby passes over into the aqueous phase as carboxylate, which is rinsed once with 200 ml of ether and is subsequently acidified in a large beaker with concentrated hydrochloric acid while being stirred. Then extraction is performed twice with 400 ml of ether in each case, and the organic phase is rinsed with water once. After drying over sodium sulphate the ether is thoroughly removed by rotating. The orange-yellow honey-like reaction product (80 g) was identified as 3-methoxycarbonyl-4-4(4-methoxyphenyl)-4-(2-naphthyl)-3-butene acid by means of the NMR spectrum.

(iii) In a 1 l flask the above reaction product is dissolved in a solution of potassium hydroxide (40 g) in roughly 600 ml of water. The brown reaction solution so formed is heated with reflux for 3 hours. After cooling the mixture is acidified with conc. hydrochloric acid while being stirred and well cooled in the ice bath. Subsequently extraction is performed twice, with 400 ml of ethyl acetate in each case. The combined ethyl acetate phases are rinsed with water once and thoroughly removed by rotating after drying over sodium sulphate. The honey-like reaction product (75 g) was identified as 3-carboxyl-4-(4-methoxy phenyl)-4-(2-naphthyl)-3-butene acid by means of the NMR spectrum.

(iv) The above-mentioned reaction product is dissolved with acetyl chloride (35 g) in 300 ml of acetic acid. The solution is heated while stirring with reflux for 2 hours. After removal of the solvent by distillation the residue is dissolved in still warm condition in roughly ml of ethyl acetate and extracted with water twice. Then extraction is performed twice, in each case with 300 ml of 5 % sodium carbonate solution. The organic phase is rinsed with water again, dried over sodium sulphate and thoroughly removed by rotation. The reaction product (65 g) is obtained as dark viscous oil and was identified as (4-methoxy phenyl-2-naphthyl methylene)succinic acid anhydride.

(v) The above-described reaction product is dissolved in roughly 600 ml of dichloro methane at room temperature and is subsequently well cooled in an ice bath. Then aluminium chloride (35 g) is added in portions while stirring and cooling well, and the mixture is allowed to thaw over night. Then the reaction mixture is poured into 1 l of ice/water for hydrolysis. After separation of the organic phase the latter is rinsed twice with 500 ml of water in each case and then extracted twice with 600 ml of 5 % sodium hydroxide solution. After washing the combined aqueous-alkaline phases with 250 ml of ether acidification is performed with conc. hydrochloric acid while stirring. Extraction takes place twice with 400 ml of ethyl acetate in each case, and the organic phase is rinsed with water, dried over sodium sulphate and thoroughly removed by rotating it. What remains is a brown solid residue (45 g) which was identified as 3-(4-methoxyphenyl)-6,7-benzindenone-2-acetic acid by means of the NMR spectrum. The isomer 6-methoxy-3-(2-naphthyl)-indenone-2-acetic acid, which would theoretically also be formed, could not be detected.

(vi) the above reaction product is suspended in roughly 300 ml of acetic anhydride. After the addition of sodium acetate (20 g) the mixture is heated up to reflux while being stirred. The product settles in thick form during cooling. After cooling down to room temperature (and additionally in the refrigerator for a short time) the soft crystalline orange-brownish precipitate so formed is evacuated and rinsed with a small quantity of acetic anhydride until the filtrate does no longer flow off in dark-brown colour. Then the product is thoroughly rinsed with water and dried at 60° C. The product (a solid of brilliant orange colour; 30 g) was identified as 11-acetoxy-9-methoxy-dibenzo[a,g]fluorene-13-on by means of the NMR spectrum.

(vii) The above-mentioned reaction product is suspended in 400 ml of ethanol and mixed with potassium hydroxide (25 g). The reaction mixture is heated up to reflux for 1.5 hours while stirring, with a wonderful intensive green colour appearing gradually. After cooling roughly half of the ethanol quantity is removed by rotation and the remaining residue is heated together with 1 l of water on the heating plate until an intensively green solution has formed. Then the solution is removed from the heating plate and acidified, in still hot condition, with conc. hydrochloric acid. An umber-brown suspension is produced which is cooled down to room temperature while being stirred. The suspension is exhausted and carefully rinsed with water. The substance removed by the suction filter is still sludgy and is sucked to dryness as thoroughly as possible at the diaphragm pump. After drying at 60° C. the umber-coloured product (25 g) was identified as 11-hydroxy-9-methoxy-dibenzo[a,g] fluorene-13-on by means of the NMR spectrum.

(viii) 3 g of the above reaction product are suspended in roughly 300 ml of toluene, together with 4-methoxy-benzophenone acetylide (4 g; produced from 4-methoxy benzophenone and sodium acetylide). After the addition of a spatula tip of 4-toluene sulfonic acid the reaction mixture is heated with reflux for 1.5 hours. In the course of the reaction the initially poorly soluble naphthol product is more and more strongly dissolving; a red-brown mixture is forming. After short cooling the toluene is removed by rotating under vacuum and the residue is dissolved in 40 ml of dichloromethane and subjected to column chromatography with aluminium oxide (water percentage 3%) as stationary phase and with a dichloro-methane/hexane mixture (2:1) as mobile phase. For final purification the raw product is digested and slightly heated in roughly 100 ml of methanol. After cooling the suspension so created is exhausted, rinsed with methanol and dried. The dark product (3 g) was identified as 6-methoxy-3-(4-methoxyphenyl)-3-phenyl-13-oxo-benz[p]indeno[2,1-f]-naphtho(1,2-b]pyrane.

(ix) 1 g of the above reaction product is dissolved in 50 ml of absolute THF while stirring and cooled in an ice bath. Lithium aluminium hydride is added in small portions until the colour of the reaction solution does no longer brighten up. Stirring is then continued for another 10 min. and the solution is poured into water, acidified with conc. hydrochloric acid until the phases are clear whereupon the organic phase is isolated. After extraction with water, drying over sodium sulphate and removal of the solvent by rotation a brownish viscous residue remains which crystallises when methanol is added. The suspension is stirred at room temperature for some minutes more and then the precipitate is exhausted. The slightly brownish solid (0.8 g) was identified as 6-methoxy-3-(4-methoxy phenyl)-3-phenyl-13-hydroxy-benz[p]indeno[2,1-f]naphtho[1,2-b]pyrane by means of the NMR spectrum. Both in solution and in the glass a green photochromy can be observed.

EXAMPLE 2

The process is performed in analogy with Example 1, only in step (ix) 1 g of the reaction product from step (viii) is dissolved in 50 ml of absolute THF at room temperature while stirring. 2 equivalents of a phenyl magnesium chloride solution are added to this solution and the mixture is stirred at room temperature for 1 hour. Then the solution is poured into water, acidified with conc. hydrochloric acid until the phases are clear, and then the organic phase is isolated. After extraction with water, drying over sodium sulphate and removal of the solvent by rotation a dark brown oil remains which crystallises when methanol is added. The suspension is stirred for some minutes more at room temperature and then the precipitate is exhausted. The beige solid (0.7 g) was identified as 6-methoxy-3-(4-methoxy phenyl)-3,13-diphenyl-13-hydroxy-benz[p]indeno[2,1-f]naphtho[1,2-b] pyrane by means of the NMR spectrum.

EXAMPLE 3

The steps (i) to (vi) of this Example were carried out on the basis of the article by F. G. Baddar, L. S. El-Assal and V. B. Baghos, published in J. Chem. Soc. 1958, p. 986, with some modifications.

(i) to (vi) In analogy with Example 1, step (ii), with 4-methoxy benzophenone (50 g) as starting material. 3-methoxycarbonyl-4-(4-methoxy phenyl)4-phenyl-3-butene acid (75 g) is formed which, in analogy with Example 1, steps (iii) to (v) is processed further to obtain a mixture of 3-(4-methoxy phenyl)-indenone-2-acetic acid and 6-methoxy-3-phenyl-indenone-2-acetic acid. The isolation of the isomers is achieved by hot digestion in benzene. After cooling and exhaustion of the suspension pure 3-(4-methoxy phenyl)-indenone-2-acetic acid is obtained as residue in the form of orange-yellow crystals (25 g) which were identified by means of the NMR spectrum. These crystals were reacted, in analogy with Example 1, steps (vi) to (vii) to obtain 5-hydroxy-3-3methoxy-7H-benzo[c]fluorene-7-on (20 g) which was obtained as red-violet powder and identified by means of the NMR spectrum.

(viii) The reaction, in analogy with Example 1, step (ix), with the above product furnishes 6-methoxy-3-(4-methoxy phenyl)-3-phenyl-13-hydroxy-indeno[2,1-f]-naphtho[1,2-b] pyrane (beige powder; 0.7 g) which was identified by means of the NMR spectrum.

EXAMPLE 4

The process is performed in analogy with Example 3, only in step (viii) 1 g of the reaction product from step (vii) is dissolved in 50 ml of absolute THF while stirring. 2 equivalents of ethyl magnesium chloride solution are added to this solution, and the combined solution is stirred at room temperature for 1 hour. Then the solution is poured into water, acidified with conc. hydrochloric acid until the phases are clear and then the organic phase is separated. After extraction with water, drying over sodium sulphate and removal of the solvent by rotation a dark brown oil remains which crystallises when methanol is added. If the product does not crystallise it is stirred in the ice bath until crystals are precipitated. The suspension is then stirred for some more minutes at room temperature, whereupon the precipitate is exhausted and the residue is rinsed subsequently with methanol. The brownish solid (0.5 g) so formed was identified as 6-methoxy -3-(4-methoxy phenyl)-3-phenyl-13-ethyl-13-hydroxy-indeno[2,1-f]naphtho[1,2-b]pyrane using the NMR spectrum.

EXAMPLES 5 TO 9

The processes are performed in analogy with Example 4, only phenyl magnesium chloride in Example 5,
1-naphthyl magnesium bromide in Example 6,
2-methyl phenyl magnesium bromide in Example 7,
2,5-dimethyl phenyl magnesium bromide in Example 8, and
3-methyl-2-thienyl magnesium bromide in Example 9 are used instead of ethyl magnesium chloride.

The products (mostly beige powders) were identified as 6-methoxy-3-(4-methoxy phenyl)-3-phenyl-13-hydroxy-indeno[2,1-f]naphtho[1,2-b]pyranes substituted with the corresponding Grignard residue at the C-13 position, using the NMR spectra.

EXAMPLE 10

The processes aperformed in analogy with Example 3, only in step (vii) the reaction is carried out with 4-diphenyl amino benzophenone acetylide (produced from 4-diphenyl amino benzophenone (B. Staskun, J. Org. Chem., 1968, 33, 3031) and sodium acetylide) instead of 4-methoxy benzophenone acetylide. The solution is heated with reflux for 3 hours. The product is 6-methoxy-3-phenyl-3-(4-diphenyl amino phenyl)-13-oxo-indeno[2,1-f]naphtho[1,2-b]pyrane as dark-red solid which was identified by means of the NMR spectrum. This substance is reacted, in analogy with Example 4, in step (viii) with a phenyl magnesium hloride solution (in analogy with Example 2) instead of the ethyl magnesium chloride solution. 6-methoxy-3,13-diphenyl-3-(4-diphenyl amino phenyl)-indeno[2,1-f]naphtho[1,2-b]-pyrane is obtained as light-grey solid which was identified by means of the NMR spectrum.

EXAMPLE 11

The process is performed in analogy with Example 3, with the variation that 6-methoxy-3,3-bis(4-methoxy phenyl)-13-oxo-indeno[2,1-f]naphtho[1,2-b] is used as starting material instead of 6-methoxy-3-(4-methoxy phenyl)-3-phenyl-13-oxo-indeno[2,1f]naphtho[1,2-b]pyrane. 6-methoxy-3,3-bis (4-methoxy phenyl)-13-butyl-13-hydroxy-indeno[2,1-f] naphtho[1,2-b]pyrane (0.6 g) is produced as brownish solid which was identified by means of the NMR spectrum.

EXAMPLES 12 TO 15

The processes are performed in analogy with Example 11, only phenyl magnesium chloride in Example 12,
1-naphthyl magnesium bromide in Example 13,
2-methyl phenyl magnesium bromide in Example 14, and
2,5-dimethyl phenyl magnesium bromide in Example 15 are used instead of butyl magnesium chloride.

The products (mostly beige powders) were identified as 6-methoxy-3,3-bis(4-methoxy phenyl)-13-hydroxy-indeno [2,1-f]naphtho[1,2-b]pyranes substituted with the corresponding Grignard residue at the C-13 position, using the NMR spectra.

EXAMPLE 16

The process is performed in analogy with Example 1, steps (ii) to (ix), however in step (ii) the reaction is carried out with benzophenone as starting material, in step (viii) with 4,4'-dimethoxy benzophenone acetylide instead of 4-methoxy benzophenone acetylide, and in step (ix) with a phenyl magnesium chloride solution (in analogy with Example 2) instead of lithium aluminium hydride. 3,3-bis (4-methoxy phenyl)-13-hydroxy-13-phenyl-indeno[2,1-f] naphtho[1,2-b] pyrane (0.6 g) is obtained as brownish solid which was identified by means of the NMR spectrum.

EXAMPLE 17

The process is performed in analogy with Example 16, however with 2.5 dimethyl phenyl magnesium bromide instead of phenyl magnesium chloride. 3,3-bis(4-methoxy phenyl)-13-(2,5-dimethyl phenyl)-13-hydroxy-indeno[2,1-f]naphtho[1,2-b]pyrane (0.5 g) is isolated as beige solid which was identified by means of the NMR spectrum.

Production of the test specimens:

500 ppm of the respective photochromic dye are dissolved in the employed monomer (TRANSHADE-150 from the company of Tokuyama; index of refraction 1.52) at room temperature while stirring. After the addition of an initiator of the alkyl peroxy-ester type (1.5% by weight) degassing is performed twice and subsequently the polymerisation is carried out in correspondence with the temperature programme recommended by the Tokuyama company. The glass casting moulds are coloured in black so that the entirety of the photochromic dyes may be integrated into the matrix in a non-excited state. After completion of the polymerisation process the test specimens are additionally tempered at 100° C. for 2 hours.

Plotting of the kinetics graphs:

For the determination of the brightening rates the test specimens so produced were measured in a common kinetics test bench (irradiation with 50 klux in compliance with EN 1836, item 6.1.3.1.1). The exposure time was 15 minutes in each case, brightening takes place in the dark. During exposure and brightening the transmission graph—evaluated by the sensitivity to brightness of the human eye, V λ—is recorded. The glass temperature is controlled via a cuvette designed for being controlled by means of a thermostat.

What is claimed is:

1. A photochromic naphthopyran dye corresponding to formula (I):

wherein

R$_1$ and R$_2$ are each independently selected from the group f consisting of (C$_1$–C$_6$)-alkyl, (C$_1$–C$_6$)-alkoxy, chloro and fluoro;

or the group consisting of hydrogen, (C$_1$–C$_6$)-cyclo-alkyl, phenyl, benzyl, dialkyl-(C$_1$–C$_6$)-amino, dicyclohexylamino, diphenylamino, piperidyl, morpholinyl and pyridyl; and m and n each independently represent 0, 1 or 2;

or two groups R$_1$ and/or two groups R$_2$ form together, independently of each other, a carbocyclic or heterocyclic ring selected from the group consisting of benzene, pyridine, pyrazine, pyrimidine, furan and thiophene;

R$_4$ is selected from the group g consisting of hydrogen, hydroxy, (C$_1$–C$_6$)-alkyl, (C$_5$–C$_6$)-cycloalkyl, (C$_1$–C$_6$)-acyl, (C$_1$–C$_6$)-alkoxy, phenyl, benzyl, phenyl mono-substituted with (C$_1$–C$_6$)-alkyl or (C$_1$–C$_6$)-alkoxy, and benzyl mono-substituted with (C$_1$–C$_6$)-alkyl or (C$_1$–C$_6$)-alkoxy;

or from mono-chloro or mono-fluoro substituted phenyl, naphthyl, phenanthryl, pyrenyl, chinolyl, isochinolyl, benzofuranyl, thienyl, benzothienyl, dibenzofuranyl, dibenzothienyl, carbazolyl or indolyl, each unsubstituted or mono-substituted with a substituent selected from the group consisting of chloro, fluoro, (C$_1$–C$_6$)-alkyl, and (C$_1$–C$_6$)-alkoxy;

or from phenyl di- or tri-substituted with substituents selected from the group consisting of chloro, fluoro, (C$_1$–C$_6$)-alkyl, (C$_1$–C$_6$)-alkoxy, (C$_1$–C$_6$)-ω-phenylalkyl and (C$_1$–C$_6$)-ω-phenoxy-alkyl with the phenyl ring at the ω-position optionally representing the X, X' or R$_4$ radical of another photochromic pyran system;

X and X' are each independently selected from the group z consisting of (a) and (b), wherein (a) consists of the un-, mono-, di- and tri-substituted aryl groups phenyl and naphthyl; and (b) consists of the un-, mono-, di- and tri-substituted heterocyclic groups pyridyl, furanyl, benzofuran-2-yl, benzofuran-3-yl, thienyl, benzothien-2-yl and benzothien-3-yl, the substituents in (a) and (b) being selected from:

the group h consisting of hydroxy, amino, mono-(C$_1$–C$_6$)-alkylamino, di-(C$_1$–C$_6$)-alkylamino, piperidino, morpholino, pyrryl; -(C$_1$–C$_6$)-alkyl, -(C$_1$–C$_6$)-chloro-alkyl, -(C$_1$–C$_6$)-fluoro-alkyl, -(C$_1$–C$_6$)-alkoxy, mono-(C$_1$–C$_6$)-alkoxy-(C$_1$–C$_4$)-alkyl, chloro and fluoro;

or the group a consisting of non-basic amines selected from the group consisting of unsubstituted or substituted diarylamino, pyrazole, imidazole, indole, pyridine, pyrazoline, imidazoline, pyrroline, phenothiazine, phenoxazine, phenazine, acridine, or carbazole, wherein the substituents on the substituted non-basic amines are selected from the group consisting of (C$_1$–C$_6$)-alkyl, (C$_1$–C$_4$)-alkoxy, phenyl, fluoro, chloro and bromo;

or X and X' are selected from (c) (C$_1$–C$_6$)-alkyl, (C$_1$–C$_6$)-chloroalkyl, (C$_1$–C$_6$)-fluoroalkyl, mono-(C$_1$–C$_6$)-alkoxy-(C$_1$–C$_4$)-alkyl, (C$_3$–C$_6$)-cycloalkyl, mono-(C$_1$–C$_6$)-alkoxy-(C$_3$–C$_6$)-cycloalkyl, chloro-(C$_3$–C$_6$)-cycloalkyl, and fluoro-(C$_3$–C$_6$)-cycloalkyl;

or

X and X' together with the carbon atom at the junction with the pyran form a saturated C$_5$–C$_{10}$-monocyclic, C$_7$–C$_{12}$-bicyclic or C$_7$–C$_{12}$-tricyclic hydrocarbon ring or a fluorene-9-ylidene;

or either X or X' is mono- or di-substituted phenyl which is substituted in the position para to the connection site with -phenyl, —(CH$_2$)$_p$-phenyl or —O—(CH$_2$)$_p$—O-phenyl substituent, wherein p represents an integer from 1 to 6, and the ring of the substituent group forms part of a second photochromic pyran; and Y is selected from the group consisting of hydrogen, (C$_1$–C$_6$)-alkyl, (C$_1$–C$_6$)-acyl, unsubstituted benzoyl, unsubstituted naphthoyl, benzoyl mono-substituted with (C$_1$–C$_6$)-alkyl or (C$_1$–C$_6$)-alkoxy, and naphthoyl mono-substituted with (C$_1$–C$_6$)-alkyl or (C$_1$–C$_6$)-alkoxy;

with the proviso that R$_1$ and R$_2$ are not from the group f if R$_4$ is from the group g, and X and X' are from the group z, and the members of the group z are unsubstituted or are substituted with substituents from the group h.

2. A photochromic naphthopyran dye according to claim 1, wherein $R_4$ comprises a heterocyclic group joined to the naphthopyran system via a carbocyclic ring.

3. A photochromic naphthopyran dye according to claim 1, wherein X and X' are selected from the group z.

4. A photochromic naphthopyran dye according to claim 1, wherein two groups $R_1$ or two groups $R_2$, independently of each other, form a carbocyclic or heterocyclic ring selected from the group consisting of benzene, pyridine, pyrazine, pyrimidine, furan and thiophene.

5. A photochromic naphthopyran dye according to claim 1, wherein at least one of X or X' represents a radical from group z which is substituted with at least one non-basic amine from group a.

6. A photochromic naphthopyran dye according to claim 5, wherein X and X' each represent the same radical from group z with different substituents.

7. A photochromic naphthopyran dye according to claim 5, wherein the substituents on X and X' are identical.

8. A photochromic naphthopyran dye according to claim 1, wherein $R_4$ is selected from the group consisting of phenyl radicals substituted at least in the ortho position, 1-naphthyl, 2-naphthyl, 9-phenanthryl, pyrenyl and heteroaromatic groups selected from benzofuranyl, benzothienyl, chinolyl or isochinolyl.

9. A photochromic naphthopyran dye according to claim 1, wherein at least one methoxy group is present at the 5-, 6-, 7- or 8-position of the naphthopyrane ring.

10. A photochromic naphthopyran dye according to claim 1, wherein each molecule of said dye contains a plurality of photochromic color centers.

11. A photochromic naphthopyran dye according to claim 10, wherein one of said plurality of photochromic color centers absorbs at a shorter or longer wavelength than another of said plurality of color centers.

12. A photochromic naphthopyran dye according to claim 1, corresponding to formula (II):

wherein
$R_1$, $R_2$, m and n have the meanings given in claim 1,
$R_5$ represents the substituents defined for $R_4$=phenyl;
o represents 0, 1, 2 or 3, and
$R_3$ is a non-basic amine from the group a.

13. A photochromic naphthopyran dye according claim 12, wherein said non-basic amino substituent is an unsubstituted or substituted diarylamino group, and at least one aryl ring is mono-, di- or tri-substituted with at least one substituent selected from the group consisting of $(C_1-C_4)$-alkyl, $(C_1-C_4)$-alkoxy, phenyl, fluoro, chloro and bromo.

14. A photochromic naphthopyran dye according to claim 1, selected from the group consisting of:

6-methoxy-3-(4-methoxyphenyl)-3,13-diphenyl-13-hydroxy-benz[p]indeno[2,1-f]naphtho[1,2-b]pyran, 6-methoxy-3-(4-methoxyphenyl)-3-phenyl-13-(2,5-dimethylphenyl)-13-hydroxybenz[p]indeno[2,1-f]naphtho[1,2-b]pyran, 3-(4-diphenylaminophenyl)-3-phenyl-13-(2,5-dimethylphenyl)-13-hydroxybenz[p]indeno[2,1-f]naphtho[1,2-b]pyran, 3-(4-diphenylaminophenyl)-6-methoxy-3,13-diphenyl-13-hydroxyindeno[2,1-f]naphtho[1,2-b]pyran, 3-(4-diphenylaminophenyl)-6-methoxy-3-phenyl-13-(2,5-dimethylphenyl)-13-hydroxyindeno[2,1-f]naphtho[1,2-b]pyran, 6-methoxy-3-(4-methoxyphenyl)-3-phenyl-13-(2,5-dimethylphenyl)-13-hydroxy-indeno[2,1-f]naphtho[1,2-b]pyran, 6-methoxy-3-(4-methoxyphenyl)-3-phenyl-13-(1-naphthyl)-13-hydroxyindeno[2,1-f]naphtho[1,2-b]pyran, 6,11-dimethoxy-3-(4-methoxyphenyl)-3-phenyl-13-(2,5-dimethylphenyl)-13-hydroxyindeno[2,1-f]naphtho[1,2-b]pyran, 3-(4-methoxyphenyl)-3-phenyl-13-(2,5-dimethylphenyl)-13-hydroxyindeno[2,1-f]naphtho[1,2-b]pyran, and 6-methoxy-3-(4-methoxyphenyl)-3-phenyl-13-(3-methyl-2-thienyl)-13-hydroxyindeno[2,1-f]naphtho[1,2-b]pyran.

15. A method of producing a photochromic naphthopyran dye according to claim 1, said method comprising the steps of:

reacting a substituted or unsubstituted benzene or naphthalene compound by Friedel-Crafts acylation to form a benzo- or naphthophenone compound A;

carrying out a Stobbe condensation of the compound A by means of a succinodiester to form an isomer mixture of semi-esters B;

hydrolyzing the semi-esters B with aqueous alkali to form an isomer mixture of diacids C;

heating the diacids C with acetyl chloride with removal of water to form an isomer mixture of cyclic anhydrides D;

reacting the anhydrides D with aluminium chloride with intramolecular 5-ring cyclization to form an isomer mixture E and isolating the isomers by solubility fractionation in benzene;

reacting the respective isomers with acetanhydride with intramolecular 6-ring cyclization to form an ester F;

subjecting the ester F to alkaline hydrolysis to form a hydroxyfluorenone derivative G;

reacting the compound G with a 2-propin-1-ol derivative to form a photochromic indeno-annellated naphthopyran dye H;

subjecting the dye H to a Grignard reaction with a Crignard reagent $R_4MgHal$ to form the compound J, wherein $R_4$ has the meaning given in claim 1, and Hal represents a halide ion; and optionally converting free hydroxyl groups in compound J to a derivative to form a compound K.

16. A method according to claim 15, wherein the Grignard reagent used to react the dye H contains a photochromic group.

17. A method according to claim 15, wherein the 2-propin-1-ol derivative used to react the dye G contains a photochromic group.

18. A method according to claim 15, wherein the photochromic naphthopyran dye contains a plurality of photochromic color centers.

19. A photochromic article comprising a light permeable matrix having applied thereto or dispersed therein at least one photochromic naphthopyran dye according to claim 1.

20. A photochromic article according to claim 19, wherein said photochromic article is selected from the group consisting of lenses, protective glasses, sighting shields in protective helmets, windows, eyeglasses, protective screens, covers, and roofs.

21. A photochromic article comprising a synthetic resin and at least one photochromic naphthopyran dye according to claim 1.

22. A photochromic article according to claim 21, wherein said synthetic resin is selected from the group consisting of poly($C_1$–$C_{12}$-alkyl methacrylates) poly(oxyalkylene dimethacrylates), polyalkoxylated phenol methacrylates, cellulose acetate, cellulose triacetate, cellulose acetate propionate, cellulose acetate butyrate, poly(vinylacetate), polyvinyl alcohol, polyvinyl chloride), polyvinylidene chloride, thermoplastic polycarbonates, polyesters, polyurethanes, polyethylene terephthalate, polystyrene, poly (α-methyl styrene), styrene/methyl methacrylate copolymers, styrene/acrylonitrile copolymers, polyvinyl butyral, and polymers and copolymers of at least one monomer selected from the group consisting of polyol(allyl carbonate) monomers, polyfunctional acrylate monomers, polyfunctional methacrylate monomers, diethylene glycol dimethacrylate monomers, ethoxylated bisphenol-A-dimethacrylate monomers, diisopropenyl benzene monomers, ethylene glycol bis-methacrylate monomers, ethoxylated phenol methacrylate monomers, alkoxylated polyalcohol acrylate monomers and diallylidene pentaerythritol monomers.

23. A photochromic article according to claim 21, wherein the synthetic resin is an opaque or transparent homo- or co-polymer selected from the group consisting of poly (methyl methacrylate), poly(ethylene glycol bis-methacrylate), poly(ethoxylated bisphenol-A-dimethacrylate), thermoplastic polycarbonate, poly (vinylacetate), polyvinylbutyral, polyurethane or a polymer or copolymer of at least one monomer selected from the group consisting of diethylene glycol bis-(allyl carbonate) monomers, diethylene glycol dimethacrylate monomers, ethoxylated phenol methacrylate monomers, diisopropenyl benzene monomers and ethoxylated tri-methylol propane triacrylate monomers.

24. A photochromic article according to claim 21, further comprising at least one further organic photochromic dye having an activated absorption maximum in the range from about 400 to 700 nm.

25. A photochromic article according to claim 21, wherein said at least one photochromic naphthopyran dye is present in a total quantity of from about 0.05 to about 2.5 mg per $cm^2$ of surface of the synthetic resin.

26. A photochromic article according to claim 21, wherein said photochromic naphthopyran dye is dispersed throughout said synthetic resin.

27. A photochromic article according to claim 21, wherein said photochromic naphthopyran dye is diffused into a surface of said synthetic resin.

* * * * *